(12) United States Patent
Moser et al.

(10) Patent No.: US 9,199,039 B2
(45) Date of Patent: Dec. 1, 2015

(54) PUSHER WITH A COUPLING ELEMENT

(75) Inventors: Ulrich Moser, Heimiswil (CH); Christian Schrul, Burgdorf (CH); Jürg Hirschel, Aarau (CH)

(73) Assignee: TecPharma Licensing AG, Burgdorf (CH)

( * ) Notice: Subject to any disclaimer, the term of this patent is extended or adjusted under 35 U.S.C. 154(b) by 889 days.

(21) Appl. No.: 12/171,061

(22) Filed: Jul. 10, 2008

(65) Prior Publication Data
US 2009/0054850 A1 Feb. 26, 2009

Related U.S. Application Data

(63) Continuation of application No. PCT/CH2007/000019, filed on Jan. 15, 2007.

(30) Foreign Application Priority Data

Jan. 17, 2006 (DE) .......... 10 2006 002 383
Feb. 1, 2006 (DE) .......... 10 2006 004 562

(51) Int. Cl.
| A61M 5/315 | (2006.01) |
| A61M 5/24 | (2006.01) |
| A61M 5/31 | (2006.01) |
| A61M 5/50 | (2006.01) |

(52) U.S. Cl.
CPC ......... *A61M 5/31535* (2013.01); *A61M 5/2448* (2013.01); *A61M 5/3146* (2013.01); *A61M 5/3156* (2013.01); *A61M 5/3158* (2013.01); *A61M 5/31511* (2013.01); *A61M 5/31553* (2013.01); *A61M 5/31571* (2013.01); *A61M 5/31591* (2013.01); *A61M 5/502* (2013.01)

(58) Field of Classification Search
CPC . A61M 5/24; A61M 5/3158; A61M 5/31553; A61M 5/31563; A61M 5/14566; A61M 5/31525; A61M 5/3155; A61M 5/31536; A61M 5/31571; A61M 5/31578; A61M 5/31591; A61M 5/31535; A61M 5/2448; A61M 5/31511; A61M 5/3146; A61M 5/3156; A61M 5/502
USPC .......................... 604/207–211, 220, 224, 228
See application file for complete search history.

(56) References Cited

U.S. PATENT DOCUMENTS

| 4,820,287 A | 4/1989 | Leonard |
| 4,968,299 A | 11/1990 | Ahlstrand et al. |
| 5,279,586 A | 1/1994 | Balkwill |
| 5,480,387 A | 1/1996 | Gabriel et al. |
| 5,536,249 A | 7/1996 | Castellano et al. |

(Continued)

FOREIGN PATENT DOCUMENTS

| DE | 603401 | 10/1934 |
| DE | 1053143 | 3/1959 |

(Continued)

*Primary Examiner* — Emily Schmidt
*Assistant Examiner* — Lauren M Peng
(74) *Attorney, Agent, or Firm* — Dorsey & Whitney, LLP; Stuart R. Hemphill, Esq.

(57) ABSTRACT

An injection device including a pusher, a dosing element and a coupling element, the pusher being displaceable in an injection direction and having at least one holding or detent area, e.g. a toothed area, for detachably holding the pusher relative to the injection device, wherein the coupling element positions the pusher relative to the dosing element for fixing the axial position of the pusher relative to the dosing element.

18 Claims, 7 Drawing Sheets

(56) References Cited

U.S. PATENT DOCUMENTS

| | | | |
|---|---|---|---|
| 5,679,111 A | 10/1997 | Hjertman et al. | |
| 5,807,346 A * | 9/1998 | Frezza | A61M 5/31553 604/208 |
| 6,193,698 B1 | 2/2001 | Kirchhofer et al. | |
| 6,235,004 B1 | 5/2001 | Steenfeldt-Jensen et al. | |
| 6,663,602 B2 | 12/2003 | Moller | |
| 6,793,646 B1 | 9/2004 | Giambattista et al. | |
| 7,169,133 B2 | 1/2007 | Broennimann et al. | |
| 7,771,399 B2 * | 8/2010 | Burren et al. | 604/211 |
| 2001/0009990 A1 | 7/2001 | Hostettler | |
| 2002/0173752 A1 | 11/2002 | Polzin | |
| 2004/0019333 A1 | 1/2004 | Graf et al. | |
| 2004/0108339 A1 | 6/2004 | Hansen et al. | |
| 2004/0186441 A1 | 9/2004 | Graf et al. | |
| 2004/0186442 A1 | 9/2004 | Graf et al. | |
| 2005/0090782 A1 | 4/2005 | Marshall et al. | |
| 2005/0137571 A1 | 6/2005 | Hommann | |
| 2005/0209570 A1 | 9/2005 | Moller | |
| 2005/0222540 A1 | 10/2005 | Kirchhofer | |
| 2008/0009807 A1 | 1/2008 | Hommann | |

FOREIGN PATENT DOCUMENTS

| | | |
|---|---|---|
| DE | 3030239 C2 | 2/1982 |
| DE | 197 30 999 C1 | 12/1998 |
| DE | 101 60 393 | 6/2003 |
| DE | 102 32 158 A1 | 2/2004 |
| DE | 102 48 061 A1 | 5/2004 |
| DE | 101 63 325 B4 | 7/2005 |
| DE | 10 2004 004 310 | 8/2005 |
| EP | 0 373 321 A1 | 6/1990 |
| EP | 897 729 | 2/1999 |
| EP | 0 713 403 B1 | 12/1999 |
| WO | WO 00/62839 A | 10/2000 |
| WO | WO 2005102421 A1 * | 11/2005 |

* cited by examiner

Fig. 1A
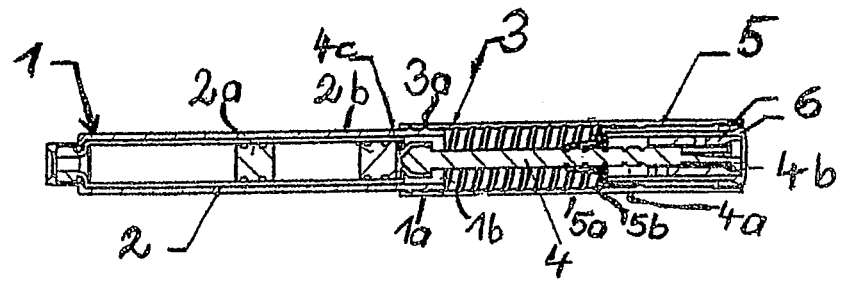
Fig. 1B
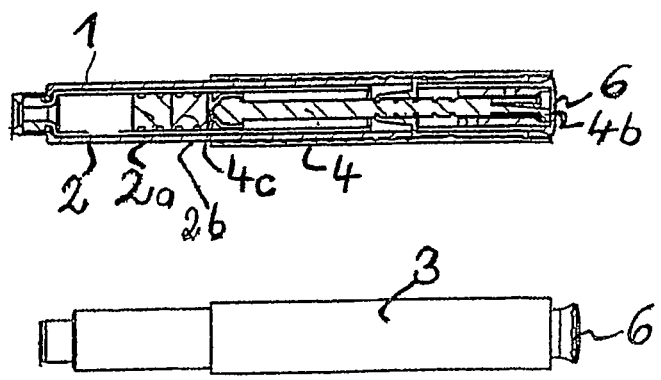
Fig. 1C
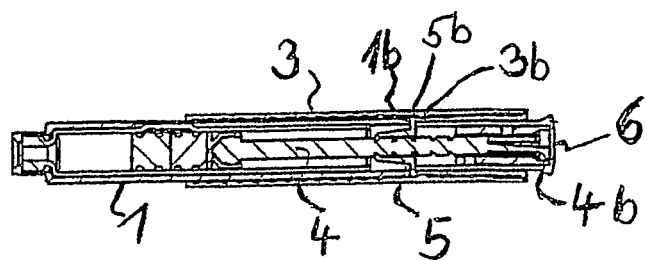

Fig. 1D
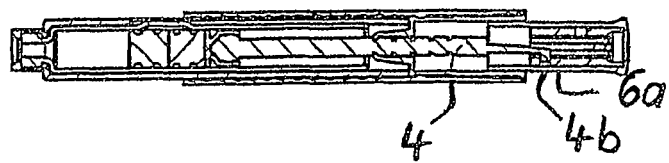
Fig. 1E
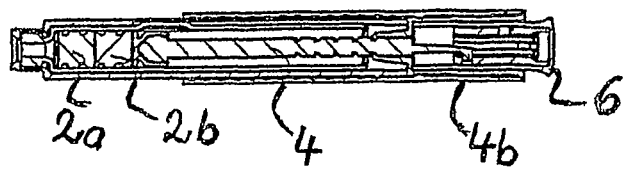

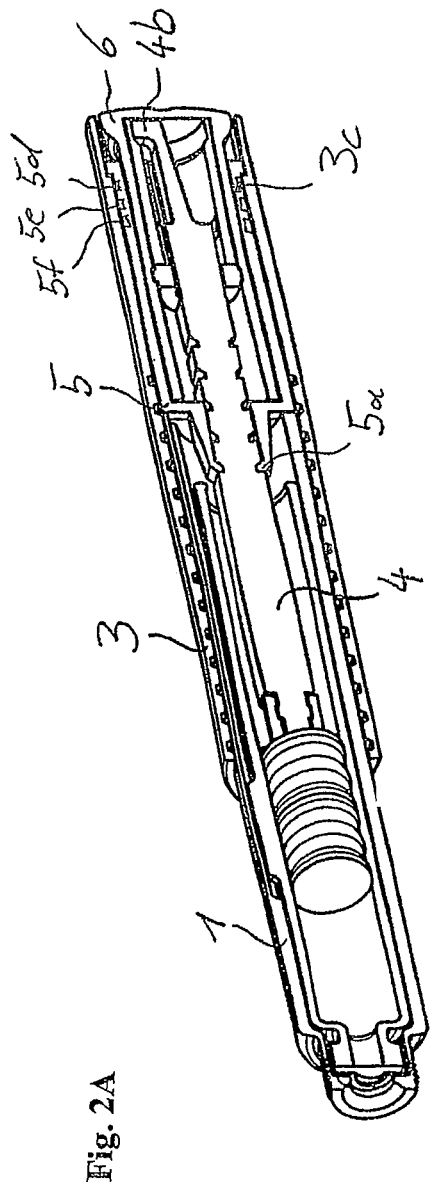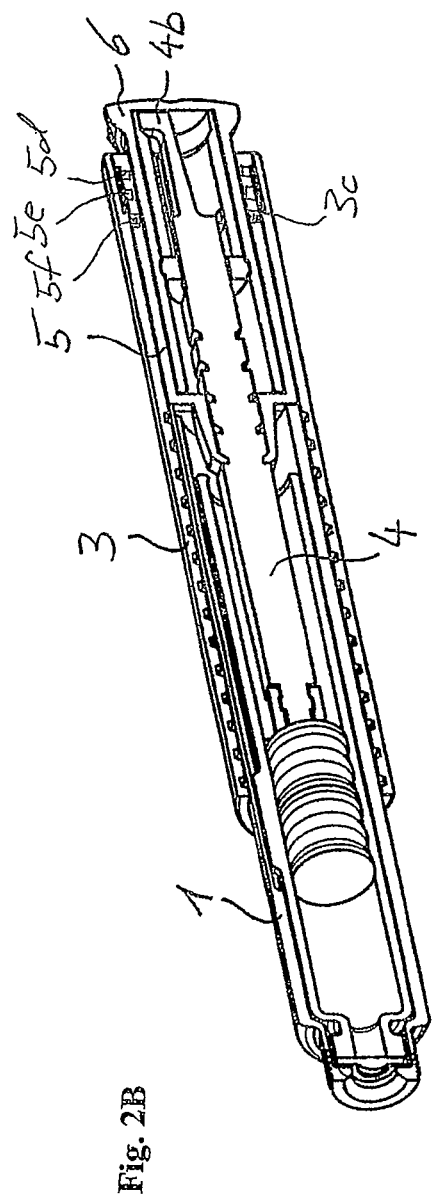
Fig. 2A
Fig. 2B

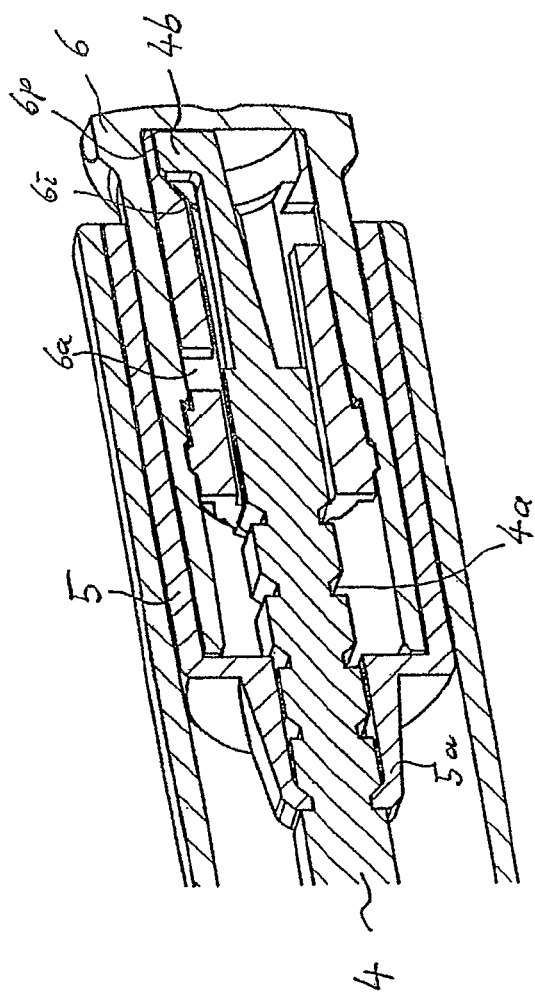
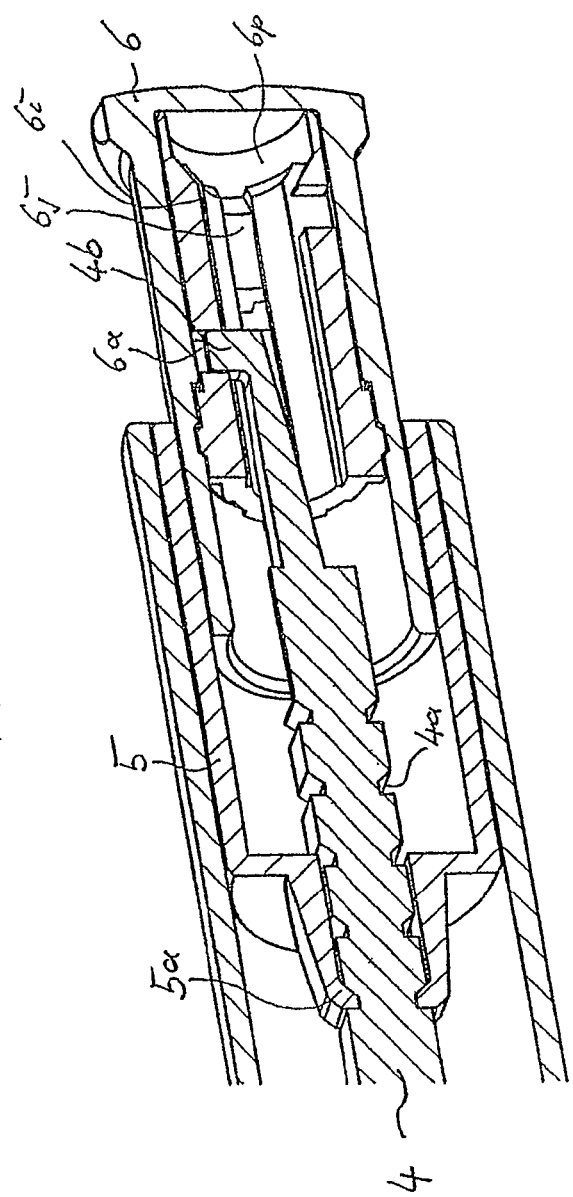
Fig. 3A
Fig. 3B

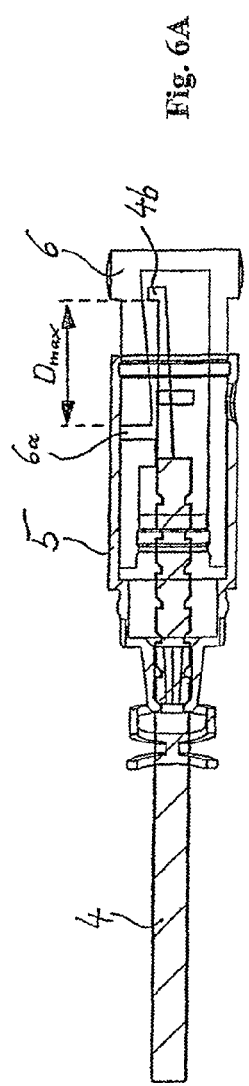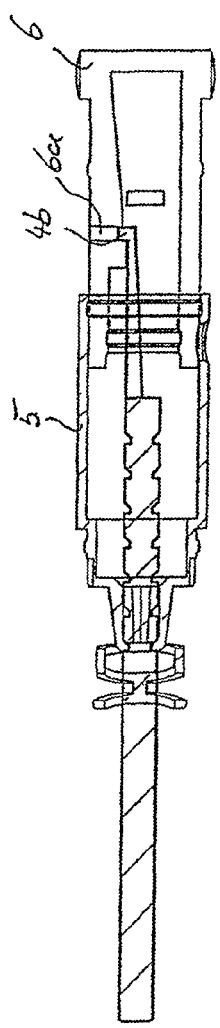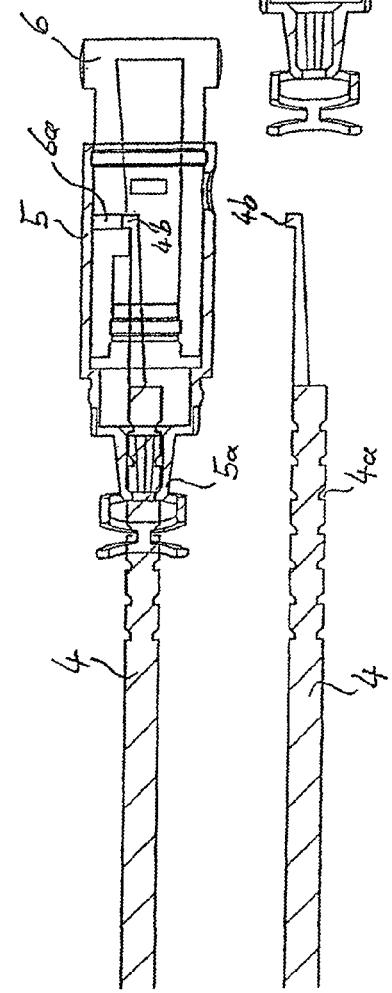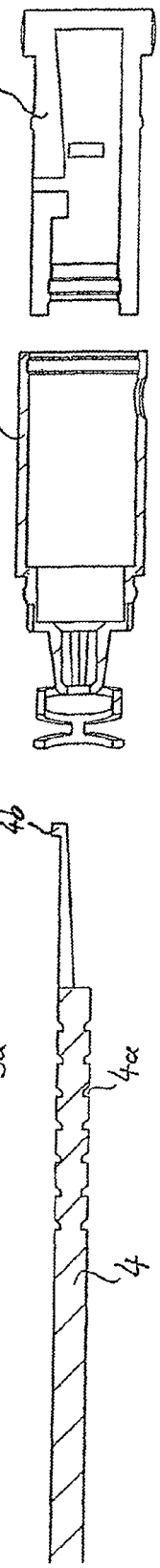

PUSHER WITH A COUPLING ELEMENT

CROSS-REFERENCED RELATED APPLICATIONS

This application is a continuation of International Patent Application No. PCT/CH2007/000019 filed Jan. 15, 2007, which claims priority to German Patent Application No. DE 10 2006 002 383.8 filed Jan. 17, 2006 and German Patent Application No. DE 10 2006 004 562.9 filed Feb. 1, 2006, the contents of all of which are incorporated in their entirety herein by reference.

BACKGROUND

The present invention relates to devices for administering, injecting, infusing, delivering or dispensing a substance or product, and to methods of making and using such devices. More particularly, it relates to a device for administering a substance, e.g. an injection device or an injection pen, which has a dose setting or selecting element for administering a set dose of an injectable product. In some embodiments, the injection device may be used for self-administering the product, e.g. in the form of a disposable injector, and may be used with a single-chamber or two-chamber ampoule.

Injection pens are widely used due to their size and shape, which makes them easy to handle when self-administering medicaments. Particularly if self-administering a medicament, such as insulin or a hormone, ease of handling, accuracy of the set dose and safety when setting the dose are of major importance.

Patent specification DE 10 2004 004 310, filed by the owner of the present application, discloses an injection device with a dose setting element, which effects a forward driving movement relative to the housing of the injection device in a forward drive direction and a dose setting movement in the direction opposite the forward driving movement and is coupled with a conveying mechanism so that the forward driving movement causes a conveying movement of the conveying mechanism, and the length of a distance defining the dose to be dispensed which is travelled by the dose setting element during the forward driving movement is set by the dose setting movement. A first catch mechanism is formed by the housing in a sleeve portion surrounding by the dose setting element and a second catch mechanism is formed by the dose setting element or a separate, additional dose setting catch body, and a catch engagement of the catch mechanisms can be released by a dose setting movement of the dose setting element or the separate, additional dose setting catch body without involving a rotating movement.

U.S. Pat. No. 5,807,346 discloses a measuring instrument for dispensing different doses of a liquid, which has a reservoir for accommodating the liquid, a displaceable toothed rack element axially disposed inside and a pushing element which can be operated by the user. Annular notches are provided on the toothed rack element and the housing has various axial slots distributed across its periphery. An outwardly projecting pin is provided on the pushing element, which is able to locate in one of the axial slots of the housing, and the setting element can be easily extracted by the user.

Patent specification EP 0 713 403 B1 discloses a syringe with a barrel, which defines or has a cylinder, the cylinder having a nozzle at one end and enclosing a plunger which is able to slide in the longitudinal direction inside the cylinder. The distance by which the plunger is able to move inside the cylinder defines the volume administered by the syringe, and the plunger is drivingly coupled with a slide which is disposed so that it moves parallel with the plunger, and the distance in length by which the plunger is able to slide inside the cylinder is defined by the movement restrictions of a stop surface on the barrel or the slide by reference to end stops on the slide or barrel. The syringe can be locked in a state in which the stop surface and the end stops are able to move only within movement limits with respect to one another, which can be selected from two or more pre-selectable predefined movement limits, and the stop surface has an insert which can be inserted from an orifice in the barrel or slide so that it projects out from it and is difficult to remove from them or can be so only by using a special tool, and the projecting part of the insert acts as a stop surface, and the position of each such orifice relative to the end stops defines one of the predefined movement distances.

SUMMARY

One object of the present invention is to provide an injection device which improves ease of setting while simultaneously reducing the likelihood of incorrect operation.

In one embodiment, the present invention comprises an injection device comprising a pusher, a dosing element and a coupling element, the pusher being displaceable in an injection direction and having at least one holding or detent area, e.g. a toothed area, for detachably holding the pusher relative to the injection device, wherein the coupling element positions the pusher relative to the dosing element for fixing the axial position of the pusher relative to the dosing element.

In one embodiment, the present invention comprises an injection device comprising a pusher that can be displaced relative to the direction of injection or relative to a support of the injection device in only the distal direction, said pusher having at least one holding or detent area, especially a toothed area for detachably holding the pusher on or in the injection device or support. The invention is characterized by a coupling element for positioning the pusher relative to a dosing element, especially for fixing the axial position of the pusher relative to the dosing element.

By virtue of one aspect of the present invention, an injection device in accordance with the present invention has a holder device for a substance to be administered, into which the substance to be administered can be introduced directly or into which a container, for example an ampoule, can be inserted. In the latter situation, the holder device is designed as an ampoule holder. The holder device can be moved relative to the injection device and an element of the injection device constituting the holder or ampoule holder can be pushed into or screwed into it or a part of it, for example into the housing of the injection device, so that if using a known two-chamber ampoule, the substances contained in the two-chamber ampoule are mixed during the pushing-in or screwing-in operation and can thus be prepared for administering to a patient. A dose selecting, setting or dose setting element is also provided, for example a rotating knob, for setting the dose of substance to be administered from the injection device, and the quantity or dose of the substance to be administered can be selected or fixed on the basis of a rotary position of the dose setting element. In an initial state, the dose setting element is pushed so far into the injection device in accordance with the present invention that it cannot be gripped by a user or can be so only with great difficulty and can not be easily pulled out.

In some embodiments, the holder device for the substance to be dispensed which can be introduced into or pushed into the injection device, for example a screw-in or push-in ampoule holder, is coupled with the dose setting element so that as the substance holder device is being pushed into or having been completely or almost completely pushed into the injection device or into a housing, the setting element is at lest partially pushed out of the injection device or a housing thereof so that it can now be operated by a user to set a dose, for example. The dose setting or setting element may be provided in the form of a rotatable dose setting knob of a type known per se, which is disposed at the proximal (or rear) end of the injection device and fixedly connected to, for example, a dose setting knob sleeve which can be pushed axially inside the injection device and can be pushed out of it to push out the dose setting knob, thereby releasing it in readiness for setting a dose.

In some preferred embodiments, the dose setting element may be coupled with the injection device so that it can not be rotated when the injection device is in the pushed-in state and can only be rotated once pushed out to set a dose. Specific details of the design of the dose setting system may be found in the explanations given herein below. The dose setting element may be designed so that after setting the dose to be administered in a pre-set defined position extracted from the injection device in which it can be rotated to set the dose, it can be extracted farther out of the injection device to load the injection device, in which case the dose setting element may be locked to prevent rotation during the extra extraction operation or alternatively also rotatable. Another option is one whereby the dose is not set until after the dose setting element has been loaded or extracted from the injection device and the dose setting element is not locked to prevent rotation until it is pushed back into the injection device to administer the substance.

In some embodiments, in the initial state or in the pushed-in state, the setting element may be retained in the injection device or a housing of the injection device by static friction or a catch mechanism, and the force of the static friction or the catch mechanism can be overcome by pushing in the substance holder device, such as the ampoule holder, to extract the setting element from the injection device. For example, a proximal face of the substance holder element or a setting element-extraction element disposed on it may move into contact with the setting element or dose setting element or may be connected to or coupled with the dose setting element by one or more other elements locked relative to the injection device, for example a guide sleeve, by a releasable catch mechanism or holder, so that a pushing-in or screwing-in movement of the substance holder device causes the setting or dose setting element to be pushed out. A catch element or some other blocking element may also be provided, which holds the dose setting element in the injection device in the pushed-in state and can be released from the substance holder element directly or from an element coupled with it to enable the dose setting element to be pushed out.

In some preferred embodiments, a plunger rod or toothed rack is provided in the injection device so that a proximal stopper or displacement body provided in the substance holder device or in an ampoule is pushed into the injection device relative to the substance holder region during the operation of pushing in or screwing in the substance holder device. In other words, the proximal stopper or displacement body is pushed into the ampoule, as a result of which, in the case of a two-chamber ampoule, mixing of the components contained in the two-chamber ampoule is initiated and then terminated when the plunger rod or toothed rack has been pushed sufficiently far in so that the two-chamber ampoule is mixed and/or in readiness for preparing to administer the substance.

In some preferred embodiments, the coupling between the substance holder element and setting or dose setting element is designed so that the dose setting element is not pushed out of the injection device until the substance holder element has been completely or almost completely inserted or introduced for fully or almost fully mixing the substances contained in the two-chamber ampoule. It may be that the dose setting element is not coupled with the substance holder element until the last part of the insertion path, for example the last 6 mm, and the dose setting element is not pushed out of the injection device until after coupling, once the proximal end of the substance holder element has made contact with the dose setting element having travelled the remaining insertion distance of 6 mm, so that the dose setting element can be gripped by a user and rotated to set the dose or pulled out farther to prime the pen.

It is of advantage to provide a marking on the dose setting element, e.g. on the circumferential face of the dose setting knob or a dose setting knob sleeve, which may be marked to assist with setting a dose and indicate dose units. This dose display may be printed on or applied to the dose setting element so that it is not visible until the dose setting element has been pushed out, in which case the dose setting element is pushed so far out that the dose display can be seen by a user, or the display printed on the dose setting element is pushed into the region of a viewing widow disposed in the housing of the injection device thereby rendering it visible.

In some embodiments, the present invention comprises a method for preparing an injection device for administering a dose of substance, wherein a dose setting element pushed into the injection device can not be gripped by a user or can be gripped only with great difficulty until after it pushed out or extended from the injection device is not pushed out of the injection device until during or after loading or pushing a substance holder element such as an ampoule holder or an ampoule into the injection device so that the setting or dose setting element can not be gripped and operated by a user until then.

By virtue of another aspect, the present invention relates to an injection device with a housing and a substance dispensing element which can be moved relative to the housing to force a substance contained in the injection device out of the injection device for dispensing by moving the dispensing element, e.g. by pushing the dispensing element into the injection device. For purposes of the present invention, at least one blocking or locking element is provided in the injection device, which, when a substance has been dispensed from the injection device once by the dispensing element, prevents another dose from being administered by the dispensing element. The dispensing element may be coupled with a dose setting or setting element or may be the does element so that, for example, a dose is set by a rotation of the dispensing element, the injection device is primed by pulling out the dispensing element and the substance is actually dispensed by pushing the dispensing element in. In some embodiments, the dispensing element may also be a rotating or dose setting knob of the injection device. The dispensing element may likewise be a housing part of the injection device which is able to move relative to another element or housing part of the injection device.

In some preferred embodiments, a blocking, or catch or lock, element is provided on the dispensing element, for example a catch cam and/or a groove, which, during or after a dispensing operation, is able to establish a connection with a co-operating complementary element, in other words a co-operating groove or catch cam of the injection device or an ampoule. In some preferred embodiments, the connection can not be released or can be released only with great difficulty once a set dose has been dispensed from the injection device.

The blocking or catch element may co-operate with a plunger rod or toothed rack of the injection device, for example, and the complementary element may be a catch element disposed on a flexible arm, for example, such as a catch cam, extending into the dispensing element, with which a positive connection can be established between the dispensing element and the toothed rack or plunger rod once the substance has been dispensed. The dispensing element can then no longer be moved relative to the toothed rack or plunger rod. The dispensing element may also be blocked or locked relative to the injection device or a housing thereof, for example by a catch connection, during or after a dispensing operation, to prevent another dispensing operation. Another option is to lock or block only a movement of the dispensing element in a specific direction, for example an axial movement and/or a rotating movement, to prevent any possibility of more substance being dispensed from the injection device due to the locked direction(s) of movement.

With respect to methods in accordance with the present invention for dispensing a substance from the injection device or for blocking or locking the injection device, a dispensing element triggering or causing dispensing of the substance may be blocked or locked before, during or after dispensing a set dose of the substance to be administered so that the dispensing element can no longer be moved in the direction which would trigger further dispensing of the substance from the injection device.

This being the case, a quantity or dose of the substance to be dispensed set or pre-set once by a user can be dispensed from the injection device one time only using the injection device and method in accordance with the present invention, and any further dispensing of the substance can be blocked or prevented, even if there is a quantity of substance to be administered left in the injection device. This is useful if mixing substances in two-chamber ampoules, particularly if the quality of the substances or mixture thereof can deteriorate or change to the extent that it would not be advisable and could possibly be damaging to the health if another injection were administered too long after mixing the substances.

BRIEF DESCRIPTION OF THE DRAWINGS

FIGS. 1A to 1E show the sequence involved in setting a dose and dispensing a substance based on an embodiment of an injection device in accordance with the present invention, seen respectively in plan view and in cross-section;

FIGS. 2A and 2B provide a view in cross-section of an injection device before and after extracting the dose setting knob;

FIGS. 3A and 3B illustrate a first embodiment of a dose setting and dispensing mechanism in cross-section;

FIGS. 6A to 6C illustrate how a dispensing mechanism in accordance with the present invention co-operates with one embodiment of a toothed rack; and FIG. 6D is an exploded diagram of the toothed rack and dispensing mechanism.

DETAILED DESCRIPTION

Figure 4A:
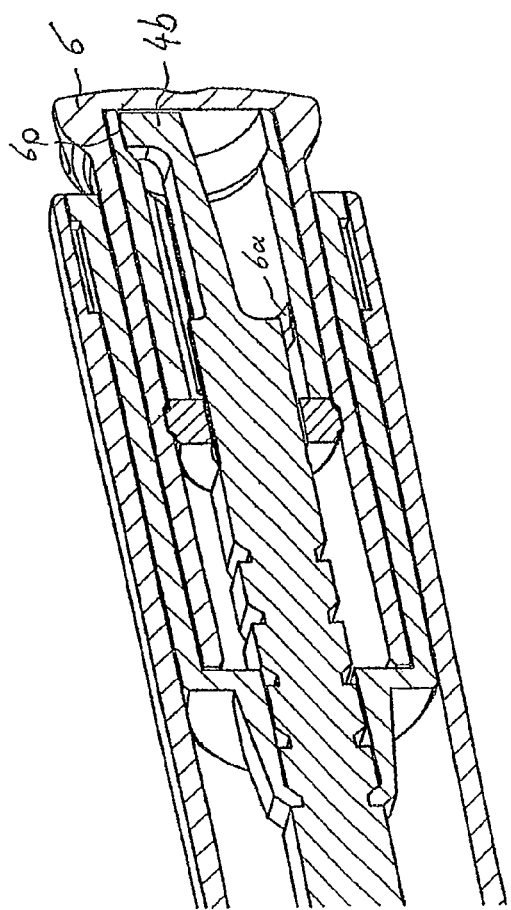
FIGS. 4A and 4B illustrate another embodiment of a dose setting and dispensing mechanism in cross-section.

FIG. 1A is a plan and cross-sectional view illustrating one embodiment of an injection device in accordance with the present invention, with an ampoule holder 1 serving as a substance holder, in which a two-chamber ampoule 2 incorporating two displaceable stoppers 2a and 2b can be fitted. The ampoule holder 1 is displaceable relative to the housing of the injection device which, in the embodiment illustrated, is provided in the form of threaded sleeve 3, and can be screwed into the internal thread 3a of the threaded sleeve 3 due to an engagement with the external thread 1a provided on the proximal end of the ampoule holder 1.

A guide sleeve 5 is connected to the threaded sleeve 3 by the annular web 3c provided on the internal face of the threaded sleeve 3 locating in the circumferentially extending groove 5d (see FIG. 2A) on the external face of the guide sleeve 5. The sleeve 5 has catch elements 5a biased radially inwardly at its distal end which locate in co-operating grooves or teeth 4a of a toothed rack 4 which is prevented from rotating by axially extending grooves, for example, securing it so that it cannot move in the proximal (rearward) direction. However, the toothed rack 4 can be moved in the distal (forward or injection) direction relative to the guide sleeve 5, and the catch elements 5a provided on elastic arms slide out of the grooves or teeth 4a of the toothed rack and snap into a subsequent groove or tooth 4a.

In the embodiment illustrated, a dose setting knob serving as a dispensing and dose setting element 6 is provided at the proximal (rear) end, which is pushed so far into the housing or into the threaded sleeve 3 that it can not practically be gripped by a user. When the injection device is in the position illustrated in FIG. 1A, which may also be termed the delivery position, only the ampoule holder 1 can be moved, in other words screwed into the threaded sleeve 3, to mix the substances contained in the two-chamber ampoule 2. However, it is not yet possible to effect a setting operation by the dose setting knob 6.

FIG. 1B shows the injection device illustrated in FIG. 1A, but in the mixing position after the ampoule holder 1 has been screwed into the threaded sleeve 3. By pushing the ampoule 2 retained by the ampoule holder 1 in the proximal direction, the shoulder 4c seated on the front face of the toothed rack 4 is moved into the ampoule 2, as a result of which the adjacently lying stopper 2b is pushed into the ampoule 2 to initiate mixing in the ampoule 2 in a known manner. Priming may also take place at the same time.

As illustrated in FIG. 1C, the ampoule holder 1 may be screwed into the threaded sleeve 3 of the injection device until a proximal contact surface 1b of the ampoule holder 1 sits against the radially outer distal or front face of the guide sleeve 5. If the ampoule holder 1 is screwed farther in, the guide sleeve 5 moves in the proximal direction relative to the threaded sleeve 3 together with the ampoule holder 1 so that the catch connection 3c, 5d is released until a stop element 5b provided on the external face of the guide sleeve 5 has moved against a complementary stop element 3b on the internal face of the threaded sleeve 3, thereby restricting the turning movement of the ampoule holder 1. Due to the movement of the guide sleeve 5 in the proximal direction, the dose setting knob 6 mounted in the guide sleeve 5 is pushed in the proximal direction out of the injection device so that the dose setting knob 6 can be used to set a dose to be dispensed from the injection device. As this happens, the annular web 3c moves into engagement with the circumferentially extending grooves 5e (priming position) and 5f (end position) of the guide sleeve 5 which is pushed past by the ampoule holder 1 lying against the guide sleeve 5.

FIG. 1D shows the primed injection device with the dose setting knob 6 pulled out of the injection device until a catch element 4b disposed on the toothed rack 4 and projecting in the proximal direction latches in a catch orifice 6a provided on the internal face of the dose setting knob 6. The toothed rack 4, latched in this manner, can be pushed in the distal direction of the injection device due to a pressure applied to the dose setting knob 6, as illustrated in FIG. 1E, to push the stoppers 2a and 2b disposed in the ampoule 2 in the distal direction and dispense the already mixed medicament from the ampoule 2. When the dose setting knob 6 is pushed back into the pen or into the threaded sleeve 3, respectively, it can then no longer be moved, as explained below, and in particular can no longer be pulled out. This ensures that the injection device in accordance with the present invention can be used for a single dispensing operation only.

FIG. 2A is perspective diagram in cross-section showing the dose setting knob 6 pushed in as illustrated in the initial position. The dose setting knob can be pushed out of the injection device by turning in or pushing in the ampoule holder 1 by using the guide sleeve 5 and thus releasing it for a user; see FIG. 2B.

FIG. 3A is a perspective cross-section illustrating a first embodiment of a setting and dispensing mechanism in accordance with the present invention. In an initial position, the dose setting knob 6 is freely rotatable to select a dose. A snapper biased radially outwardly or the catch element 4b of the threaded rack 4 is able to revolve freely round the groove 6p revolving around the proximal inner face of the dose setting knob 6 so that the dose setting knob 6 can also be retained. If a dose is set by a marking applied to the external circumferential face of the dose setting knob 6, the dose setting knob 6 can be pulled out of the injection device, as illustrated in FIG. 3B, until the catch element 4b, guided by a groove 6i in the internal face of the dose setting knob 6, latches into one of several catch orifices 6a or 6b (with guide grooves 6i or 6j; see FIG. 5B) disposed in the interior of the dose setting knob 6. The set or selected dose can be dispensed by pushing in the dose setting knob 6, which drives the threaded rack 4 with it in the distal direction and pushes it relative to the guide sleeve 5 due to the positive connection. When the catch element 4b locates in or moves into the groove 6i of the dose setting knob 6, as illustrated in FIG. 3B, the dose setting knob is no longer freely rotatable, but can be moved axially in the groove 6i until it latches in the catch orifice 6a. Having been pushed into the pen, the dose setting knob 6 can no longer be moved due to this connection, and due to the catch connection. The catch connection (formed by elements 3c, 5f) between the threaded sleeve 3 and guide sleeve 5 is stronger than the catch connection (formed by elements 4a, 5a) between the guide sleeve 5 and toothed rack 4, so that a pressure applied to the dose setting knob 6 will cause the toothed rack 4 to move axially forwards relative to the guide sleeve 5.

Figure 4B:
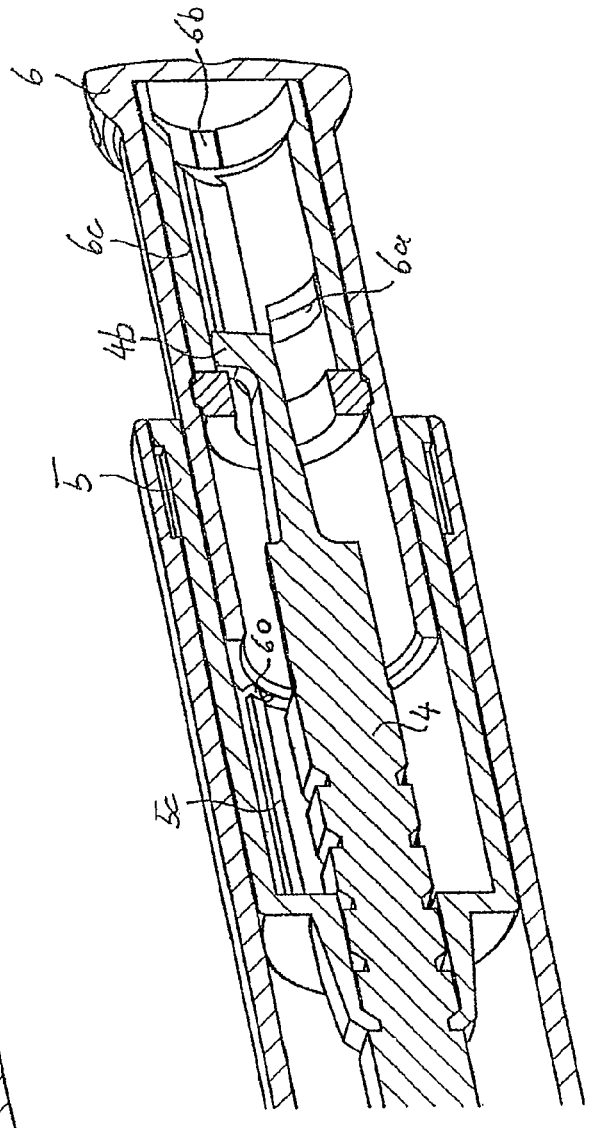

FIG. 4A, in conjunction with FIG. 4B, illustrates a second embodiment of a setting and dispensing mechanism of the present invention. In the position illustrated in FIG. 4A, the dose setting knob 6, releasably retained by the catch element 4b locating in the groove 6p, can no longer be radially rotated due to one or more guide bars 5c (see FIG. 4B) on the internal face of the guide sleeve 5 locating in co-operating grooves or indentations 6o in the external face of the dose setting knob 6.

When the dose setting knob 6 is pulled out of the injection device, as illustrated in FIG. 4B, the anti-rotation lock of the dose setting knob 6 is released by pushing the grooves 6o away from the guide bars, the catch element 4b runs through the empty groove 6c of the dose setting knob 6 into the setting groove 6q extending circumferentially round the internal face of the dose setting knob 6, and the dose setting knob 6 can be freely rotated to select the dose. The dose is set by catch points, recesses or orifices 6a, 6b, 6m, 6n on the internal face of the dose setting knob 6 disposed axially offset from one another in the circumferential direction cooperating with co-operating guide grooves 6i to 6l (see FIG. 5B) of differing length. When the dose setting knob 6 is pushed in, the catch element 4b moves along the guide groove 6i, 6j, 6k or 6l fixed by the rotary position of the dose setting knob 6 until it latches on the co-operating catch point 6a, 6b, 6m or 6n. When the dose setting knob 6 is pushed farther in, it drives the toothed rack 4 coupled via the catch connection of the catch element 4b with it. When the dose setting knob 6 is fully pushed in, the dose setting knob 6 can no longer be moved due to the anti-rotation lock (formed by elements 5c, 6o) and the coupling with the toothed rack 4 which can no longer be pulled out in the proximal direction, so that the injection device is locked.

Figure 5A:
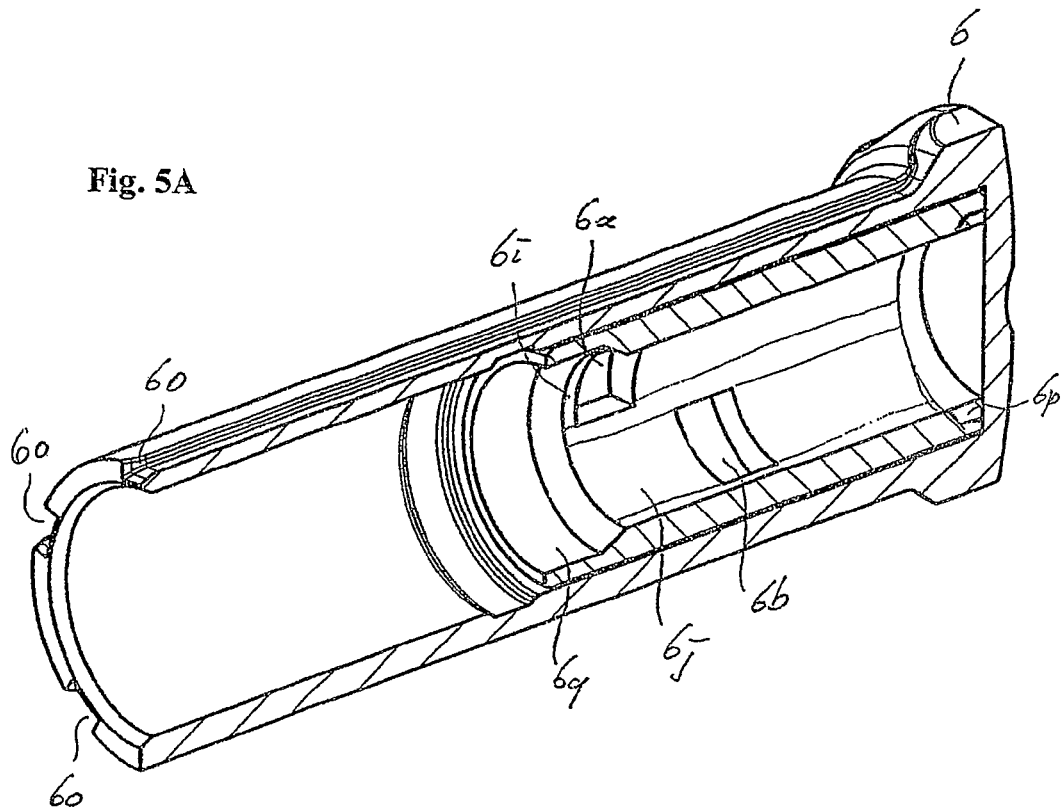
FIG. 5A is a view in cross-section showing a dose setting knob in accordance with the present invention.

FIG. 5A is a perspective view in section illustrating an embodiment of a dose setting knob 6 which may be used with both of the variants described above, with various catch orifices 6a, 6b on the internal face offset from one another in the circumferential direction and axial direction. Thus, the knob affords a latching option for the catch element 4b in one of the catch orifices 6a, 6b in each different axial direction depending on a rotary position of the dose setting knob 6. The toothed rack 4 is therefore pulled out only to the degree defined by the rotary position and the orifices 6a, 6b, 6m, 6n of the knob 6, even when the knob 6 is fully pulled out, as described in connection with the embodiment illustrated in FIG. 3. By contrast, turning to the embodiment described in connection with FIG. 4, the toothed rack is pushed in only to the degree defined by the rotary position and the orifices 6a, 6b, 6m, 6n of the knob 6.

Figure 5B:
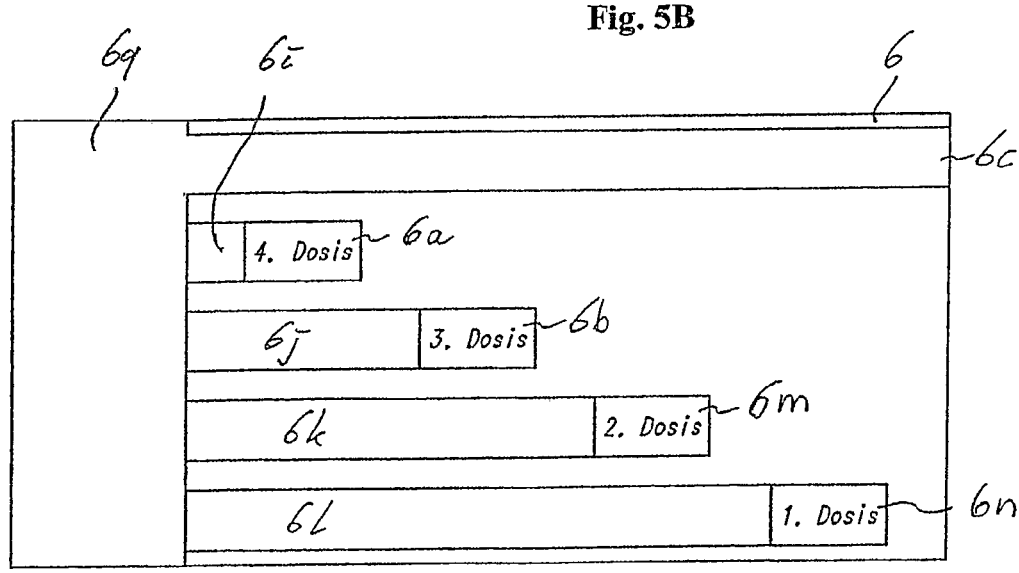
FIG. 5B is a diagram showing the internal face of the dose setting knob illustrated in FIG. 5A rolled out flat.

FIG. 5B is a diagram of the internal profile of the dose setting knob 6 rolled out flat, wherein, depending on the rotary position of the dose setting knob 6, different pushing paths of the toothed rack 4 for pushing the catch element 4b in can be predefined due to the grooves 6i to 6l of differing lengths, thereby enabling different doses to be dispensed. In FIG. 5B, "1st dose" represents the smallest and "4th dose" the biggest dose which can be predefined with the second embodiment.

FIG. 6A illustrates how the setting and dose setting mechanism co-operates with the toothed rack 4 based on the first embodiment illustrated in FIG. 3, and in the cross-sectional view in FIG. 6A, the maximum stroke or dispensing movement effected by the illustrated mechanism is denoted as the distance between the catch element 4b of the toothed rack 4 and the catch orifice 6a of the dose setting knob 6 denoted by $D_{max}$.

When the dose setting knob 6 is pulled out, as illustrated in FIG. 6B, the catch element 4b latches in the catch orifice 6a and once latched in the extracted position, the dose setting knob 6 can no longer be rotated and can be pushed in so as to dispense the dose, as illustrated in FIG. 6C. In the pushed-in position, the catch lugs 5a of the guide sleeve 5 prevent the toothed rack 4 and hence the dose setting knob 6 coupled with the toothed rack 4 from being pulled out again, so that the dose setting knob 6 is blocked in the position illustrated in FIG. 6C and the injection device can no longer be operated.

Instead of a catch or catch orifice such as described with reference to FIGS. 3 to 6, one or more stops, complementary stops, steps, projecting elements, webs or cams, for example, could also be provided on the dose setting knob 6. Likewise, the grooves 6i to 6l may be provided in the form of blind grooves or blind runs without adjoining openings.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a forward driving rod, a dose setting element and a holder, the driving rod being displaceable relative to the injection device or relative to the holder in a distal injection direction of the injection device only,
    wherein the driving rod comprises a) at least one retaining or catch region arranged at one end of the driving rod configured as a toothing for releasably retaining the driving rod on or in the injection device or holder and b) a first coupling element for positioning the driving rod relative to the dose setting element and establishing an engagement between the driving rod and the dose setting element,
    wherein the dose setting element comprises a plurality of second coupling elements engagable with the first coupling element, each of the plurality of second coupling elements configured with a dose-differentiating complementary stop, catch point, recess or orifice adapted to engage with the first coupling element for selecting one of a plurality of different doses,
    wherein the dose setting element is movable relative to the driving rod between a first position, in which the first coupling element and the plurality of second coupling elements are disengaged with each other and the dose setting element is rotatable to set a dose, and a second position, where the first coupling element is engaged with one of the plurality of second coupling elements such that displacement of the dose setting element relative to the driving rod in the injection direction is prevented and the dose setting element is prevented from rotating to set the dose,
    wherein the engagement of the first coupling element with the one of the plurality of second coupling elements in the second position blocks a second dispensing from the injection device such that the injection device can be used for only a single dispensing operation, and
    wherein the engagement of the first coupling element and the one of the plurality of second coupling elements cannot be released or can be released only with great difficulty.

2. The injection device according to claim 1, wherein the engagement of the first coupling element and the one of the plurality of second coupling elements lock the rod relative to the dose setting element in an axial position of the dose setting element in which the dose setting element is pulled out from the injection device in a direction opposite the injection direction.

3. The injection device according to claim 2, wherein the lock is releasable.

4. The injection device according to claim 1, wherein movement of the dose setting element in the injection direction drives the driving rod relative to the holder to deliver the set dose from the injection device.

5. The injection device of claim 1, wherein the injection device further comprises a catch connection formed between the holder and the injection device, wherein said catch connection is stronger than the engagement between the holder and the driving rod such that pressure applied to the dose setting element causes the driving rod to move in the injection direction relative to the holder.

6. The injection device of claim 1, wherein the retaining region prevents the driving rod from rotating axially thereby preventing the rod from displacement in the direction opposite the injection direction.

7. The injection device of claim 6, wherein as the dose setting element is pulled out of the injection device, the first coupling element moves into one of a plurality of axially extending grooves on an inner face of the dose setting element such that the dose setting element is no longer rotatable relative to the first coupling element, but can be moved axially along the groove until the first coupling element engages with one of the plurality of second coupling elements.

8. The injection device of claim 1, wherein the plurality of second coupling elements is arranged around an inner face of the dose setting element and each corresponds to a predetermined dose such that depending on a rotary position of the dose setting element, the first coupling element engages with one of the plurality of second coupling elements to set the predetermined dose.

9. An injection device comprising:
    a forward driving rod which can be displaced relative to the injection device or relative to a holder of the injection device in a distal dose delivery direction only, said rod comprising:
        at least one retaining region with teeth arranged at one end of the rod for releasably retaining the rod on or in the injection device or holder; and
        a coupling element comprising an element projecting radially outwardly; and
    a dose setting element comprising an interior in which said coupling element is arranged and a plurality of dose-differentiating catch orifices or points on an inner face configured to latch with the coupling element for selecting one of a plurality of different doses,
    wherein in an initial position of the dose setting element, the coupling element is unlatched from the catch orifices or points and the dose setting element is rotatable relative to the coupling element, and when the dose setting element is pulled out of the injection device, the coupling element latches into one of the plurality of catch orifices or points in a second position thereby preventing rotation of the dose setting element,
    wherein the latched engagement of the coupling element with one of the plurality of catch orifices or points in the second position prevents a second dispensing operation such that the injection device can be used for only a single dispensing operation, and
    wherein the engagement of the coupling element and the one of the plurality of catch orifices or points cannot be released or can be released only with great difficulty.

10. The injection device according to claim 9, wherein the coupling element blocks an axial position of the rod relative to the dose setting element.

11. The injection device as claimed in claim 9, wherein the coupling element is asymmetrical.

12. The injection device as claimed in claim 9, wherein the forward driving rod pushes directly or indirectly on a displacement body in an ampoule carried by the injection device.

13. The injection device as claimed in claim 9, wherein the dose setting element comprises recesses of differing axial lengths on the inner face of the dose setting element, said recesses offset from one another in the circumferential direction.

14. The injection device of claim 13, wherein the recesses of differing axial lengths each terminate in one of the plurality of catch orifices or points, each catch orifice or point corresponding to a predetermined dose such that depending on a rotary position of the dose setting element, the coupling element engages with one of the plurality of catch orifices or points to set the predetermined dose.

15. The injection device as claimed in claim 9, wherein the dose setting element has teeth in which the coupling element locates to set a dose.

16. The injection device as claimed in claim 15, wherein the coupling element is offset in relation to the retaining region.

17. The injection device according to claim 16, wherein the offset is in a direction opposite to the injection direction.

18. The injection device of claim 9, wherein as the dose setting knob is pulled out of the injection device, the coupling element moves into one of a plurality of axially extending grooves on an inner face of the dose setting element such that the dose setting element is no longer rotatable relative to the coupling element, but can be moved axially along the groove until the coupling element latches in one of the plurality of catch orifices or points.

* * * * *